(12) United States Patent
Kremer et al.

(10) Patent No.: US 8,383,079 B2
(45) Date of Patent: Feb. 26, 2013

(54) MOLECULAR SIEVES HAVING MICRO AND MESOPOROSITY, THEIR SYNTHESIS AND THEIR USE IN THE ORGANIC CONVERSION REACTIONS

(75) Inventors: Sebastien P. B. Kremer, Watermaal Bosvoorde (BE); Machteld Maria Mertens, Boortmeerbeek (BE); Luc R.M. Martens, Meise (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 539 days.

(21) Appl. No.: 11/713,508

(22) Filed: Mar. 2, 2007

(65) Prior Publication Data

US 2007/0244341 A1 Oct. 18, 2007

Related U.S. Application Data

(60) Provisional application No. 60/792,484, filed on Apr. 17, 2006.

(51) Int. Cl.
*C01B 33/36* (2006.01)
*C01B 39/00* (2006.01)
*C01B 39/04* (2006.01)
*C01B 15/16* (2006.01)
*C07C 211/00* (2006.01)
*B01J 27/182* (2006.01)

(52) U.S. Cl. ........ 423/700; 423/701; 423/702; 564/463; 423/305; 502/214

(58) Field of Classification Search .................. 423/306, 423/700
See application file for complete search history.

(56) References Cited

U.S. PATENT DOCUMENTS

| 4,843,977 | A | | 7/1989 | Bridges |
| 4,900,529 | A | * | 2/1990 | Sanchez et al. ............... 423/705 |
| 5,145,816 | A | | 9/1992 | Beck et al. |
| 5,849,258 | A | * | 12/1998 | Lujano et al. ................. 423/700 |
| 6,358,486 | B1 | | 3/2002 | Shan et al. |
| 6,565,826 | B2 | | 5/2003 | Jacobsen et al. |
| 6,620,983 | B1 | * | 9/2003 | Cao et al. ...................... 585/640 |

FOREIGN PATENT DOCUMENTS

| EP | 1 106 575 | 6/2001 |
| EP | 1 430 949 | 6/2004 |
| EP | 1 479 662 | 11/2004 |
| WO | WO 00/06492 | 2/2000 |
| WO | WO 00/06493 | 2/2000 |
| WO | WO 00/06494 | 2/2000 |

OTHER PUBLICATIONS

Kustova, Marina et al., Mesoporous MEL-type zeolite single crystal catalysts, Jul. 2004, Catalysis Letters, vol. 96, Nos. 3-4, pp. 205-211.*
Claus J.H. Jacobsen et al., Mesoporous Zeolite Single Crystals, J. Am. Chem. Soc., 2000, vol. 122, pp. 7116-7117.

(Continued)

*Primary Examiner* — Melvin C Mayes
*Assistant Examiner* — Bijay Saha
(74) *Attorney, Agent, or Firm* — Kevin M. Faulkner; David M. Weisberg (57) ABSTRACT

A crystalline molecular sieve comprises at least [AlO4] and [PO4] tetrahedral units and comprising a first framework structure defining a first set of uniformly distributed pores having an average cross-sectional dimension of from about 0.3 to less than 2 nanometers and further comprising a second framework structure defining a second set of uniformly distributed pores having an average cross-sectional dimension of from 2 to 50 nanometers. The first framework structure is preferably of the CHA framework type.

16 Claims, 6 Drawing Sheets

OTHER PUBLICATIONS

J.S. Beck et al., A New Family of Mesoporous Molecular Sieves Prepared with Liquid Crystal Templates, J. Am. Chem. Soc., 1992, vol. 114, pp. 10834-10843.

S.E. Dapurkar et al., Nanosized metal oxides in the mesopores of MCM-41 and MCM-48 silicates, Catalysis Today, vol. 68, 2001, pp. 63-68.

C.T. Kresge et al., Ordered mesoporous molecular sieves synthesized by a liquid-crystal template mechanism, Letters to Nature, vol. 359, Oct. 22, 1992, pp. 710-713.

H. van Bekkum et al., Studies in Surface Science and Catalysis, vol. 137, Elsevier Science, 2001, pp. 1-67.

Szostack R., "*Principles of Synthesis and Identification*," Molecular Sieve (New York, Van Nostrand Reinhold, 1989, pp. 61-68, 145-160, and 269-276.

Wilson, Stephen T., Verified Syntheses of Zeolitic Materials, "*Templating in Molecular Sieve Synethsis*", pp. 1-4 [online],[retrieved on Aug. 7, 2009]. Retrieved fro the Internet <http://www.iza-online.org/synthesis/IZA-syn_Main.htm>.

\* cited by examiner

*FIG. 4*

MOLECULAR SIEVES HAVING MICRO AND MESOPOROSITY, THEIR SYNTHESIS AND THEIR USE IN THE ORGANIC CONVERSION REACTIONS

CROSS REFERENCE TO RELATED APPLICATIONS

This claims the benefit of and priority from U.S. Ser. No. 60/792,484, filed Apr. 17, 2006. The above application is fully incorporated herein by reference.

FIELD OF THE INVENTION

This invention relates to crystalline molecular sieves having both microporosity and mesoporosity, to a method of synthesizing such materials and to their use in organic conversion reactions.

BACKGROUND OF THE INVENTION

Crystalline molecular sieves all have a 3-dimensional, four-connected framework structure of corner-sharing [TO4] tetrahedra, where T is one or more tetrahedrally coordinated cations. Examples of well known molecular sieves are silicates, which comprise [SiO4] tetrahedral units; aluminosilicates, which comprise [SiO4] and [AlO4] tetrahedral units; aluminophosphates, which comprise [AlO4] and [PO4] tetrahedral units; and silicoaluminophosphates, which comprise [SiO4], [AlO4], and [PO4] tetrahedral units.

Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pp. 1-67, Elsevier Science, B. V., Amsterdam, Netherlands (2001). For example, zeolite and zeolite-like molecular sieves are microporous materials containing pores and cavities having a size that range from a few angstroms to about 2 nanometers. In this application, the terms "micropore", "microporous," and all their derivatives refer collectively to pores having a diameter of less than 2 nanometers.

Zeolites and zeolite-like materials are characterized by their chemical composition (e.g., Si:Al atomic or molar ratios), as well as their crystal framework connectivity, conveniently described by a topological model. For a given chemical composition, an infinite number of theoretical structures is possible. Zeolites with over 130 different topologies have been synthesized, characterized and assigned a three letter code as mentioned in the *Atlas of Zeolite Framework Types,* 5th edition, Elsevier, London, England (2001).

Zeolites and zeolite-type materials are widely used in separation processes (ion exchange, selective sorption). In their acid form, zeolites and zeolite-like materials are acid catalysts, due to the combination of their strong acidity and molecular size- and shape-selectivity. Such catalytic reactions normally take place in the pores and cavities of zeolites and zeolite-type materials but intra-particle diffusion limitations and pore blocking can prevent accessibility to a large number of catalytic sites.

One way to improve the diffusion properties of a molecular sieve is to reduce the size of the molecular sieve crystals. Various methods have been described to make small crystal size molecular sieves (see, for example, International Patent Publication Nos. WO 00/06492, WO 00/06493, and WO 00/06494). However, the colloidal behavior of very small particles makes them difficult to recover and handle, especially on an industrial scale. Moreover, reducing crystal size does not address the issue of diffusion within the molecular sieve crystals.

Diffusion within molecular sieve crystals can be enhanced by the inclusion of intacrystalline mesopores, which can act as "molecular highways" to and from the active sites of the sieve thereby reducing the average intrapore diffusion distance from, for example, 1 micron, to, for example, 50 nanometers or less. This can, of course, be achieved by synthesis of molecular sieves having uniformly distributed pores all sized within the mesoporous range, such as the MCM-41 materials reported by Kresge et al., in *Nature,* 1992, 359, 710 and by Beck et al., in *J. Am. Chem. Soc.* 1992, 114, 10834. In the context of the present invention, the terms "mesopore", "mesoporous," and all their derivatives refer collectively to pores having a diameter of from 2 to 50 nanometers.

However, while such mesoporous materials offer good diffusion properties, they frequently lack the strong acidity of their microporous analogues, and, of course, the desirable shape selectivity of microporous zeolite and zeolite-like materials is lost. Therefore, various strategies have been developed to modify the physical and chemical properties of mesoporous materials. For example, U.S. Pat. No. 5,145,816 discloses post-synthesis functionalization of MCM-41 type materials. In addition, it is known to encapsulate metal oxides in the mesopores of MCM-41 materials, see, for example, Dapurkar et al., *Catalysis Today,* 68 (2001), pp. 63-68.

Various methods have also been proposed for producing molecular sieves that exhibit both microporosity and mesoporosity. For example, U.S. Pat. No. 6,358,486 describes a process for producing an inorganic oxide, such as a silicate or aluminosilicate, that contains micro- and mesopores, comprising heating a mixture comprising water, an inorganic oxide and at least one compound, such as a glycol, that binds to the inorganic oxide by hydrogen bonding. Typically, the mixture also includes a template of the type that is used for producing micropores in zeolite synthesis, such as tetramethylamonium, tetraethylammonium, tetrapropylammonium, and tetrabutylammonium salts.

In addition, U.S. Pat. No. 6,843,977 describes a porous structured aluminosilicate composition which comprises a framework of linked tetrahedral $SiO_4$ and $AlO_4$ units assembled from zeolite fragments, the framework defining pores having an average size of 1 to 100 nanometers and a Si to Al molar ratio of between about 1000 to 1 and 1 to 1, wherein the composition has at least one x-ray diffraction peak between 2 and 100 nm and retains at least 50% of its initial framework pore volume after exposure to 20 volume % steam at 800° C. for two hours. The composition is produced by assembly of a hexagonal aluminosilicate structure from seeds that would normally nucleate the crystallization of zeolite Y, ZSM-5, or zeolite beta. The seeds are heated in the presence of a surfactant, such as cetyltrimethylammonium bromide or a non-ionic PEO block copolymer, to form the mesoporous hexagonal structure.

U.S. Published Patent Application No 2001/0003117, published Jun. 7, 2001, discloses a method of preparing zeolite single crystals comprising the step of applying a synthesis gel with a zeolite precursor composition within the pore system and on the surface of a particulate matrix material having a predetermined pore structure and particle size; subjecting the precursor composition to crystallizing conditions; and isolating porous single crystals of the zeolite by removing the matrix material. The matrix material is preferably carbon black, which can be removed by controlled combustion or hydrogenation to create mesopores inside the individual large crystals.

To date, only silicates and aluminosilicates having both microporosity and mesoporosity have been reported; there have been no reports of the synthesis of aluminophosphates and silicoaluminophosphates with such bimodal pore distribution. According to the invention, it has now been found that certain microporous aluminophosphate and silicoaluminophosphate molecular sieves, in particular, those having the CHA framework type, having intracrystalline mesopores can be synthesized by growing the crystalline material around nanosized particles of a thermally decomposable material, such as carbon black.

SUMMARY OF THE INVENTION

In one aspect, the invention resides in a crystalline molecular sieve comprising at least [AlO4] and [PO4] tetrahedral units and comprising a first framework structure defining a first set of uniformly distributed pores having an average cross-sectional dimension of from 0.3 to less than 2 nanometers and further comprising a second framework structure defining a second set of uniformly distributed pores having an average cross-sectional dimension of from 2 to 50 nanometers.

Preferably, said crystalline molecular sieve also comprises [SiO4] tetrahedral units.

In a further aspect, the invention resides in a crystalline molecular sieve comprising a CHA framework-type material and having intracrystalline mesopores.

Preferably, said crystalline molecular sieve is a metalloaluminophosphate, such as a silicoaluminophosphate or aluminophosphate.

Preferably, said intracrystalline mesopores have a diameter of about 10 to about 50 nanometers. Conveniently, said crystalline molecular sieve has a mesopore volume larger than 0.1 ml/g, preferably larger than 0.2 ml/g.

In yet a further aspect, the invention resides in a method of synthesizing a crystalline molecular sieve comprising a CHA framework-type material and having intracrystalline mesopores, the method comprising:
 (a) preparing a first reaction mixture capable of forming a CHA structure-type molecular sieve;
 (b) combining said first reaction mixture with nanoparticles of a removable material inert to the conditions used in (c);
 (c) maintaining said first reaction mixture under conditions sufficient to form crystals of said molecular sieve between said nanoparticles;
 (d) removing said removable material; and
 (e) recovering said crystalline molecular sieve.

Preferably, the method further comprises:
 (i) preparing a second reaction mixture capable of forming a CHA structure-type molecular sieve;
 (ii) maintaining said second reaction mixture under conditions sufficient to form said CHA structure-type molecular sieve;
 (iii) separating said CHA structure-type molecular sieve from said second reaction mixture; and
 (iv) acidifying the second reaction mixture remaining after said separating (iii) to produce said first reaction mixture.

Preferably, said removable material comprises carbon. Conveniently, the removable material is removed by heating.

In still a further aspect, the invention resides in a process for converting an organic starting material into a product, the process comprising contacting the starting material with a catalyst comprising a crystalline molecular sieve as described herein.

In one embodiment, the process comprises the conversion of an organic oxygenate to olefins and/or alkylamines.

DESCRIPTION OF THE EMBODIMENTS

The present invention relates to a crystalline molecular sieve comprising at least [AlO4] and [PO4] tetrahedral units which define a first framework structure having a first set of uniformly distributed pores with an average cross-sectional dimension of from 0.3 to less than 2 nanometers and a second set of uniformly distributed pores with an average cross-sectional dimension of from 2 to 50 nanometers. More particularly, the invention relates to the composition and synthesis of a crystalline molecular sieve, particularly a silicoaluminophosphate or aluminophosphate, comprising a CHA framework-type material but also having intracrystalline mesopores.

The crystalline molecular sieves according to the present invention are useful as adsorbents and as catalysts in organic conversion reactions, particularly in the production of olefins or alkylamines from organic oxygenates, such as methanol and/or dimethyl ether.

Crystalline Molecular Sieve

In one embodiment, the present crystalline molecular sieve comprises at least [AlO4] and [PO4] tetrahedral units and normally at least [SiO4], [AlO4], and [PO4] tetrahedral units. In addition, the molecular sieve can contain additional metal oxide [MeO4] units, where Me is, for example, As, Be, B, Cr, Co, Ga, Ge, Fe, Li, Mg, Mn, Ti, Zn, or mixtures thereof.

In particular, the molecular sieve of said one embodiment comprises a first framework structure defining a first set of uniformly distributed micropores having an average cross-sectional dimension of from 0.3 to less than 2 nanometers and a second framework structure defining a second set of uniformly distributed mesopores having an average cross-sectional dimension of from 2 to 50 nanometers. Generally, the first set of uniformly distributed pores has an average cross-sectional dimension of from 0.3 to 1 nanometer and, more preferably, from 0.3 to 0.5 nanometer. The topology of the first framework structure can vary widely but typically will be such that the first framework structure is of the MFI, MEL, MTW, BEA, FER, TON, MTT, MFS, MOR, ITE, CHA, AEI, or intergrown CHA/AEI framework type as defined in the *Atlas of Zeolite Framework Types*, 5th edition, Elsevier, London, England (2001).

In a further embodiment, the present crystalline molecular sieve comprises a CHA framework-type material and also includes intracrystalline mesopores. The molecular sieve of the further embodiment is preferably an aluminophosphate or metalloaluminophosphate, particularly a silicoaluminophosphate.

Preferably, the mesopores in the present crystalline molecular sieve has an average cross-sectional dimension of from about 10 to about 50 nanometers.

The second set of mesopores in the present crystalline molecular sieve is uniformly distributed, which means that mesopores occur throughout the material. In this respect, the second set of pores is different from meso- or macropores that typically occur in zeolitic materials and that are often referred to as stacking faults. The presence of mesopores throughout the molecular sieve can be verified experimentally by measuring the mesopore volume of the sieve, which typically will be larger than 0.1 ml/g, preferably larger than 0.2 ml/g, such as 0.3 ml/g or more. Typically, microporous materials with stacking faults have mesopore volumes of 0.1 ml/g or less. Also, the mesopores in the present crystalline molecular sieve have a fairly narrow size distribution, such that at least 90% by volume of all mesopores are desirably within 50%, preferably within 30%, and advantageously within 20% of the average mesopore size.

The presence of the different types of pores in the crystalline material of the invention can be determined by nitrogen adsorption. The t-plot method provides the micropore volume, whereas the BJH method provides the mesopore size distribution and volume (see E. P. Barrett, L. G. Joyner, P. P. Halenda, "The determination of pore volume and area distributions in porous substances. I Computation from nitrogen isotherms", J. Am. Chem. Soc., 1951, 73, 373).

Method of Making the Crystalline Molecular Sieve

The present crystalline molecular sieve can be produced by any of the known methods for producing materials with a combination of microporosity and mesoporosity.

In particular, the molecular sieve of said further embodiment comprising a CHA framework-type material can be produced by a modification of the conventional method for producing standard, non-mesoporous SAPO-34. Thus, initially an aqueous reaction mixture capable of forming SAPO-34 is produced and is subjected to a first crystallization step to produce crystals of microporous SAPO-34. The microporous SAPO-34 crystals are then separated from the reaction mixture and discarded or diverted for alternative use and the remaining mother liquor is reactivated by acidification. After reactivation, the mother liquor is impregnated onto nanoparticles of a removable material, such as carbon black, and subjected to a second crystallization step to produce crystals of SAPO-34 between the carbon nanoparticles. The carbon-containing SAPO-34 product is then recovered from the mother liquor and, after washing and drying, the product is conveniently calcined to remove the carbon black particles and produce the desired mesoporous SAPO-34.

The initial reaction mixture is typically produced by mixing water with a source of aluminum, a source of phosphorus and, optionally, a source of silicon together with an organic directing agent for directing the synthesis of SAPO-34. Suitable sources of aluminum include aluminum salts, especially water-soluble salts, such as aluminum nitrate, as well as hydrated aluminum oxides, such as boehmite and pseudoboehmite. Suitable sources of phosphorus include phosphoric acid, organic phosphates such as triethyl phosphate, and crystalline or amorphous aluminophosphates. Suitable sources of silicon include silicates, e.g., tetraalkyl orthosilicates, fumed silica, such as Aerosil (available from Degussa), and aqueous colloidal suspensions of silica, for example, that are sold by E.I. du Pont de Nemours under the tradename Ludox.

Any organic directing agent capable of directing the synthesis of a CHA framework-type molecular sieve can be used in the initial reaction mixture. For example, suitable organic directing agents for directing the synthesis of CHA framework-type materials include adamantammonium compounds, such as N,N,N-trimethyl-1-adamantammonium compounds, N,N,N-trimethyl-2-adamantammonium compounds, and N,N,N-trimethylcyclohexylammonium compounds, N,N-dimethyl-3,3-dimethylpiperidinium compounds, N,N-methylethyl-3,3-dimethylpiperidinium compounds, N,N-dimethyl-2-methylpiperidinium compounds, 1,3,3,6,6-pentamethyl-6-azonio-bicyclo(3.2.1)octane compounds, N,N-dimethylcyclohexylamine, and the bi- and tri-cyclic nitrogen containing organic compounds cited in: (1) *Zeolites and Related Microporous Materials*: State of the Art 1994, Studies of Surface Science and Catalysis, Vol. 84, pp. 29-36; (2) *Novel Materials in Heterogeneous Catalysis* (ed. Terry K. Baker & Larry L. Murrell), Chapter 2, pp. 14-24, May 1990; (3) J. Am. Chem. Soc., 2000, 122, pp. 263-273; and (4) U.S. Pat. Nos. 4,544,538 and 6,709,644.

Alternatively, the organic directing agent can be a compound having the formula:

$$R^1R^2N-R^3$$

wherein $R^1$ and $R^2$ are independently selected from the group consisting of alkyl groups having from 1 to 3 carbon atoms and hydroxyalkyl groups having from 1 to 3 carbon atoms and $R^3$ is selected from the group consisting of 4- to 8-membered cycloalkyl groups, optionally, substituted by 1 to 3 alkyl groups having from 1 to 3 carbon atoms; and 4- to 8-membered heterocyclic groups having from 1 to 3 heteroatoms, said heterocyclic groups being, optionally, substituted by 1 to 3 alkyl groups having from 1 to 3 carbon atoms and the heteroatoms in said heterocyclic groups being selected from the group consisting of O, N, and S. Preferably, the directing agent is selected from N,N-dimethylcyclohexylamine, N,N-dimethylmethyl-cyclohexylamine, N,N-dimethylcyclopentylamine, N,N-dimethylmethyl-cyclopentylamine, N,N-dimethylcycloheptylamine, N,N-dimethylmethylcycloheptylamine, and most preferably is N,N-dimethylcyclohexylamine (DMCHA).

Typically, the initial reaction mixture has a molar composition within the following ranges:

$P_2O_5:Al_2O_3$ from about 0.5 to about 1.5,
$SiO_2:Al_2O_3$ from 0 to about 0.5,
$R:Al_2O_3$ from about 0.5 to about 2, and
$H_2O:Al_2O_3$ from about 30 to about 300, where R is the organic directing agent.

The first crystallization step is generally conducted at a temperature between about 120° C. and about 200° C., typically between about 150° C. and about 180° C., for a period of time of from about 24 to 120 hours, typically about 48 to 96 hours. The reaction mixture may be agitated or held static during the first crystallization step. As a result of the first crystallization step, crystals of SAPO-34 are formed and, when crystallization is complete, these crystals are removed from the reaction mixture, typically by centrifugation, and then discarded or set aside for alternative use.

After removal of the mesoporous SAPO-34 crystals, the remainder of the reaction mixture, referred to herein as the "mother liquor", is normally at too high a pH to allow further molecular sieve crystallization and, hence, is initially reactivated by acidification with phosphoric acid until the pH of the mother liquor is adjusted to a value of about 6.0 to about 8.0. A water-miscible low surface-tension compound, such as ethanol, is then conveniently added to the mother liquor in an amount between about 10 wt % and about 50 wt % of the acidified mother liquor to improve the wetting properties of the mother liquor.

After acidification and ethanol addition, the mother liquor is impregnated onto carbon black nanoparticles, which have previously been dried, typically by heating at a temperature between about 100° C. and about 150° C. for a period of time of from about 1 to 24 hours. Typically, the carbon black has an average particle size of about 10 nanometers to about 20 nanometers and is combined with the mother liquor in an amount between about 70 wt % and about 90 wt % based on the total weight of carbon black and mother liquor.

The mixture of carbon black and mother liquor is then subjected to a second crystallization step, generally at a temperature between about 120° C. and about 200° C., typically between about 150° C. and about 180° C., for a period of time of from about 24 to 120 hours, typically about 48 to 96 hours. The second crystallization step is conveniently effected in an autoclave with the mixture of carbon black and mother liquor being placed in a container surrounded with water to maintain saturated humidity. As a result of the second crystallization step, crystals of SAPO-34 grow between the carbon nanoparticles and, when crystallization is complete, these crystals are recovered from the reaction mixture, typically by filtration. The crystals are then washed and dried to produce an intermediate product comprising SAPO-34 containing intracrystalline carbon nanoparticles. This intermediate product can then be converted to the desired mesoporous SAPO-34 by calcination to remove the carbon. The calcination is typically conducted at a temperature between about 500° C. and about 650° C., for a period of time of from about 1 to 24 hours in the presence of an oxygen-containing gas, preferably air.

Uses of the Crystalline Molecular Sieve

Examples of suitable catalytic uses of the crystalline molecular sieve of the invention include: (a) hydrocracking of heavy petroleum residual feedstocks, cyclic stocks and other hydrocrackate charge stocks, normally in the presence of a hydrogenation component selected from Groups 6 and 8 to 10 of the Periodic Table of Elements; (b) dewaxing, including isomerization dewaxing, to selectively remove straight chain paraffins from hydrocarbon feedstocks typically boiling above 177° C., including raffinates and lubricating oil basestocks; (c) catalytic cracking of hydrocarbon feedstocks, such as naphthas, gas oils, and residual oils, normally in the presence of a large pore cracking catalyst, such as zeolite Y; (d) oligomerization of straight and branched chain olefins having from about 2 to 21, preferably 2 to 5 carbon atoms, to produce medium to heavy olefins which are useful for both fuels, i.e., gasoline or a gasoline blending stock, and chemicals; (e) isomerization of olefins, particularly olefins having 4 to 6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene, to produce ethylbenzene and cumene; (i) isomerization of dialkylaromatic hydrocarbons, such as xylenes; (j) catalytic reduction of nitrogen oxides; (k) the conversion of organic oxygenates to olefins; and (l) synthesis of monoalkylamines and dialkylamines.

One preferred use of the crystalline molecular sieve of the invention is in the catalytic conversion of organic oxygenates to one or more olefins, particularly ethylene and propylene. As used herein, the term "organic oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative organic oxygenates include lower straight chain or branched aliphatic alcohols, their unsaturated counterparts, and their nitrogen, halogen, and sulfur analogues. Examples of suitable organic oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol.

In the present oxygenate conversion process, a feedstock comprising an organic oxygenate, optionally, with one or more diluents, is contacted in the vapor phase in a reaction zone with a catalyst comprising the composite material of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example, from about 250° C. to about 800° C., including from about 250° C. to about 750° C., conveniently from about 300° C. to about 650° C., typically from about 350° C. to about 600° C., and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor), and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, such as in the range of from about 0.5 $hr^{-1}$ to about 300 $hr^{-1}$, for example, in the range of from about 0.1 $hr^{-1}$ to about 200 $hr^{-1}$.

A practical embodiment of a reactor system for the oxygenate conversion process is a circulating fluid-bed reactor with continuous regeneration, similar to a modern fluid catalytic cracker. Fixed beds are generally not preferred for the process because oxygenate-to-olefin conversion is a highly exothermic process which requires several stages with inter-coolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example, air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

In one embodiment, the catalyst is pretreated with dimethyl ether, a $C_2$-$C_4$ aldehyde composition and/or a $C_4$-$C_7$ olefin composition to form an integrated hydrocarbon co-catalyst within the porous framework of the CHA framework-type molecular sieve prior to the catalyst being used to convert oxygenate to olefins. Desirably, the pretreatment is conducted at a temperature of at least 10° C., such as at least 25° C., for example, at least 50° C., higher than the temperature used for the oxygenate reaction zone and is arranged to produce at least 0.1 wt %, such as at least 1 wt %, for example, at least about 5 wt % of the integrated hydrocarbon co-catalyst, based on total weight of the molecular sieve. Such preliminary treating to increase the carbon content of the molecular sieve is known as "pre-pooling" and is further described in U.S. Patent Application Publication Nos. 2005/0101815, 2005/0101816, and 2005/0101817, all of which were published on May 12, 2005, and are fully incorporated herein by reference.

Another preferred use of the crystalline molecular sieve of the invention is in the reaction of organic oxygenates with ammonia to produce monoalkylamines and dialkylamines, particularly methylamine and dimethylamine. Examples of suitable organic oxygenate compounds for use in this reaction include alcohols having 1 to 3 carbon atoms, specifically, methanol, ethanol, n-propanol and isopropanol, and their ether counterparts, including methyl ethyl ether, dimethyl ether, diethyl ether and di-isopropyl ether. The reaction is conducted, preferably, but not exclusively, in a flowing system in a gaseous fixed bed or fluidized bed, with the molar ratio of ammonia to oxygenate being generally from about 0.5 to about 20, such as about 1 to about 5. The reaction conditions typically include a temperature of about 200 to 400° C., such as about 250 to about 360° C., a pressure of about 0.1 to about 10 MPa, such as about 0.5 to about 2 MPa and gas hourly space velocity, GHSV, of about 100 to about 10,000 $hr^{-1}$.

The invention will now be more particularly described with reference to the Example and the accompanying drawings.

EXAMPLE 56.48 g of water was added to 26.66 g of pseudoboehmite (Condea Pural SB) in a mixer. Sequentially, 44.66 g of $H_3PO_4$ (85% in water), 9.36 g of silica sol (Ludox AS 40), and 163.10 g of tetraethylammonium (TEA) hydroxide (35% in water) were added dropwise to the pseudoboehmite suspension under stirring. The molar composition of the resultant mixture was $(SiO_2)_{0.32} (Al_2O_3)_1 (P_2O_5)_1 (TEA)_2 (H_2O)_{52}$.

The slurry was transferred to a static autoclave and heated at 170° C. for 72 hr (8 hr heating time). The product was then subjected to centrifugation (4000 rpm; 30 minutes) and the sedimented solid, SAPO-34 as derived by XRD measurement, was discarded. $H_3PO_4$ (85% in water) was added dropwise to 80.32 g of the remaining turbid liquid (the "mother liquor") until a 10-minute stable pH of 7.5 was reached. 17.14 g ethanol was then added to 40 g of the mother liquor.

14.85 g of carbon black (Cabot ASTM D-3249) was dried at 130° C. for 3 hr and then 54.26 g of the acidified mother liquor was added to the carbon black under stirring. The product was dried at room temperature for 24 hr. 18.17 g weight loss was observed.

The product was transferred to a container in an autoclave (surrounded with water around for saturated humidity) and heated at 170° C. for 72 hr under quiescent conditions (8 hr heating time). The product was then dispersed in 750 mL water under stirring for 30 minutes and recovered by filtration. The dispersion and filtration procedures were repeated three times with additional washing with 500 mL water in the last round. The resultant carbon-containing intermediate product was dried at 110° C. for 10 hr and then calcined at 600° C. for 8 hr (10 hr heating time) under flowing air atmosphere to obtain the final product. Complete carbon removal was confirmed by the white color of the final product. The product was stored in an oven at 200° C.

Figure 1:
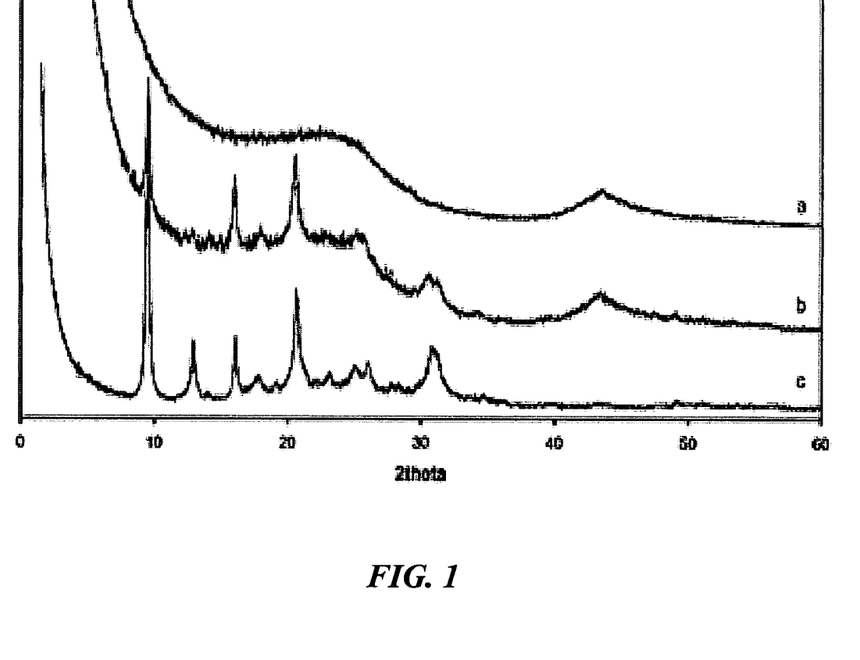
FIG. 1 gives the X-ray diffraction patterns (a) to (c) of the carbon black, the carbon-containing SAPO-34 intermediate product, and the mesoporous final product, respectively, of Example 1.

X-ray diffraction patterns of the carbon black, the carbon-containing intermediate product, and the final product are shown in FIGS. 1(a) to (c), respectively. The X-ray diffraction pattern of the intermediate product shows the typical sharp Bragg features of SAPO-34, together with the broad signals in the region 15-25 degrees 2θ and around 43 degrees 2θ due to the presence of the carbon black [FIG. 1(b)]. Upon calcination, only the diffraction peaks related to the SAPO-34 remain, although slightly altered due to the atmospheric conditions.

Figure 2A:
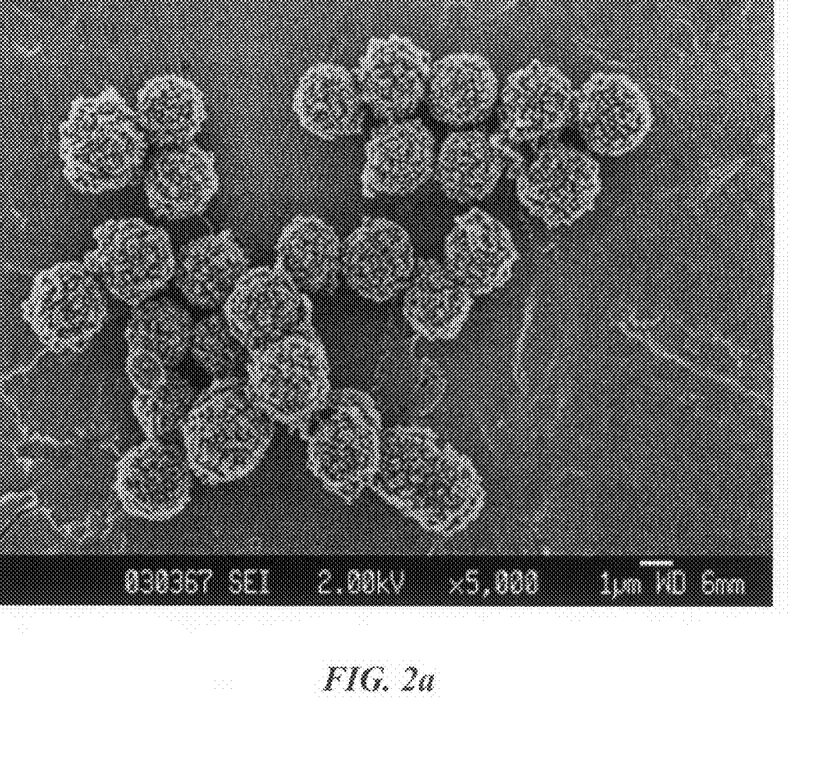
FIGS. 2(a) and 2(b) are scanning electron micrographs of the mesoporous final product of Example 1.
Figure 2B:
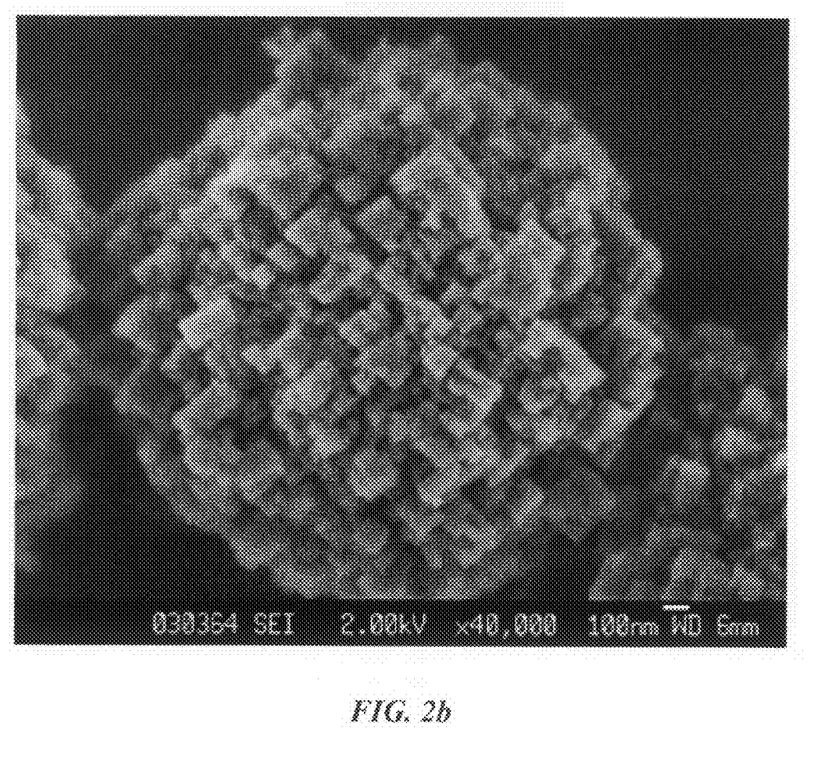

Referring to FIGS. 2(a) and 2(b), SEM images of the final product show SAPO-34 crystals with intracrystalline mesopores. The entrances to the mesopores are visible as dark cavities at the surface of the particles.

Figure 3A:
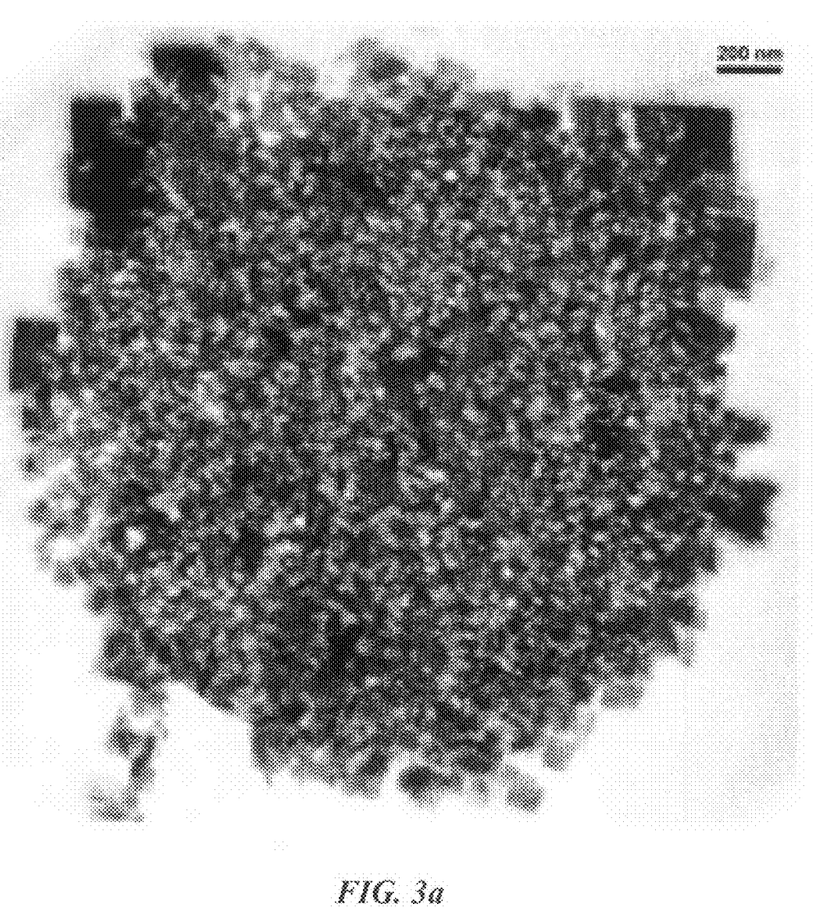
FIGS. 3(a) and 3(b) are transmission electron micrographs with an electron diffraction pattern insert of a microtomed sample of the mesoporous final product of Example 1.
Figure 3B:
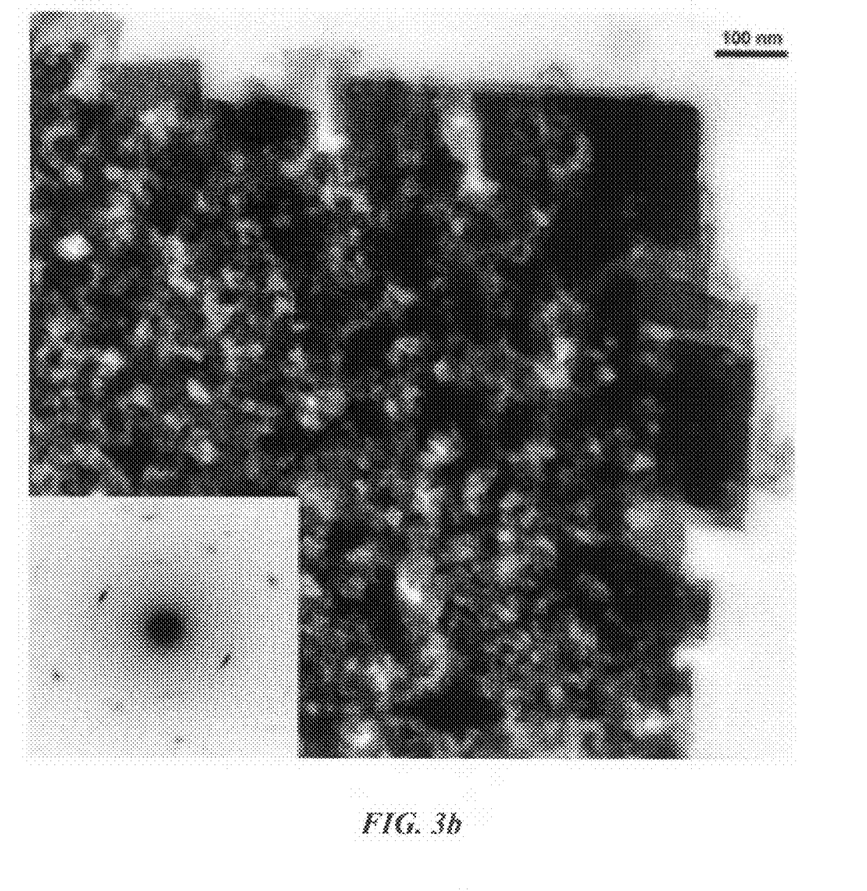

Referring to FIGS. 3(a) and 3(b), the transmission electron micrograph (TEM) image of the final product shows a SAPO-34 crystal with intracrystalline mesopores visible as the zones with darker contrast. According to the TEM image, these zones have sizes between 20 and 30 nm and are highly interconnected and homogeneously distributed through the crystal. It is clear from the electron diffraction pattern shown in the inset to FIG. 3(b) that the product comprises single crystals as opposed to agglomerated nanocrystals.

Figure 4:
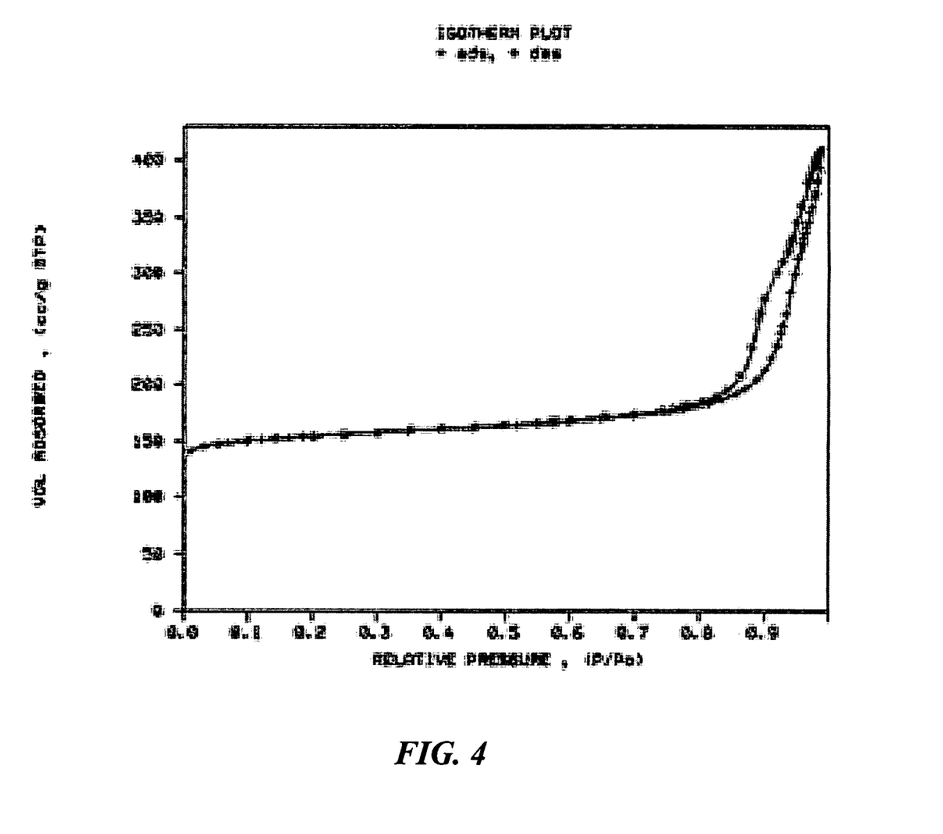
FIG. 4 is the nitrogen adsorption isotherm of the mesoporous final product of Example 1 at −196° C.

The nitrogen adsorption isotherm of the final product (FIG. 4) shows the presence of micropores (adsorption at low pressures) and mesopores (hysteresis loop at high pressures). The pore volume, surface area, and pore size are derived from BET, BJH and t-plot methodologies and are shown in Table 1.

TABLE 1

|  | Volume (ml/g) | Surface area (m²/g) | Size (nm) |
|---|---|---|---|
| Total | 0.64 | 527 | |
| Mesopore | 0.44 | 100 | 18 |
| Micropore | 0.20 | 427 | |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for converting an organic starting material into a product, the process comprising contacting the starting material with a catalyst comprising a crystalline molecular sieve comprising at least [AlO$_4$] and [PO$_4$] tetrahedral units and comprising a first framework structure defining a first set of uniformly distributed pores having an average cross-sectional dimension of from about 0.3 to less than 2 nanometers and further comprising a second framework structure defining a second set of uniformly distributed pores having an average cross-sectional dimension of from 2 to 50 nanometers, wherein the crystalline molecular sieve is first made by the process of:
   (a) in a first crystallization step, preparing a first reaction mixture comprising an organic directing agent and a source of SiO$_2$ and Al$_2$O$_3$ at a SiO$_2$ to Al$_2$O$_3$ ratio within the range from 0 to 0.5 and capable of forming a CHA structure-type molecular sieve, crystallizing the first reaction mixture, followed by removing the crystallized CHA structure-type molecular sieve from the first reaction mixture to form a mother liquor, wherein the organic directing agent can be a compound having the formula: R$^1$R$^2$N—R$^3$, wherein R$^1$ and R$^2$ are independently selected from the group consisting of alkyl groups having from 1 to 3 carbon atoms and hydroxyalkyl groups having from 1 to 3 carbon atoms and R$^3$ is selected from the group consisting of 4- to 8-membered cycloalkyl groups, optionally, substituted by 1 to 3 alkyl groups having from 1 to 3 carbon atoms; and 4- to 8-membered heterocyclic groups having from 1 to 3 heteroatoms, said heterocyclic groups being, optionally, substituted by 1 to 3 alkyl groups having from 1 to 3 carbon atoms and the heteroatoms in said heterocyclic groups being selected from the group consisting of O, N, and S;
   (b) acidifying the mother liquor having the crystallized CHA removed to a pH of about 6.0 to about 8.0 to form an acidified mother liquor, followed by combining the acidified mother liquor with nanoparticles of a removable material inert to the conditions used in (c);
   (c) in a second crystallization step, maintaining the mixture of acidified mother liquor and nanoparticles at a temperature within the range from 120 to 200° C. to form crystals of said molecular sieve between said nanoparticles;
   (d) removing said removable material; and
   (e) recovering said crystalline molecular sieve.

2. The process of claim 1, wherein the process comprises the conversion of an organic oxygenate-to-olefins or alkylamines.

3. The process of claim 1 and also comprising [MeO4] tetrahedral units where Me is an element different from phosphorus and aluminum.

4. The process of claim 1 and also comprising [SiO4] tetrahedral units.

5. The process of claim 1, wherein said first set of uniformly distributed pores having an average cross-sectional dimension of from about 0.3 to about 1.0 nanometer.

6. The process of claim 1, wherein said first set of uniformly distributed pores having an average cross-sectional dimension of from about 0.3 to about 0.5 nanometer.

7. The process of claim 1, wherein second set of uniformly distributed pores having an average cross-sectional dimension of about 10 to about 50 nanometers.

8. The process of claim 1 and having a mesopore volume larger than 0.1 ml/g.

9. The process of claim 1 and having a mesopore volume larger than 0.2 ml/g.

10. A process for converting an organic starting material into a product, the process comprising contacting the starting material with a catalyst comprising a crystalline molecular sieve comprising a CHA framework-type material and having intracrystalline mesopores, wherein the crystalline molecular sieve is first made by the process of:
   (a) in a first crystallization step, preparing a first reaction mixture comprising an organic directing agent and a source of SiO$_2$ and Al$_2$O$_3$ at a SiO$_2$ to Al$_2$O$_3$ ratio within the range from 0 to 0.5 and capable of forming a CHA structure-type molecular sieve, aging such mixture for 24 to 120 hours at a temperature within the range from 120 to 200° C., followed by removing the CHA structure-type molecular sieve from the first reaction mixture to isolate a mother liquor;
   (b) acidifying the mother liquor to a pH of about 6.0 to about 8.0, followed by combining a low surface tension compound with the mother liquor, then combining this mother liquor with nanoparticles of a removable material inert to the conditions used in (c) to form a mixture of low surface tension compound, mother liquor and nanoparticles;
   (c) in a second crystallization step, maintaining the mixture at a temperature within the range from 120 to 200° C. to form crystals of said molecular sieve between said nanoparticles;
   (d) removing said removable material; and
   (e) recovering said crystalline molecular sieve.

11. The process of claim 10, wherein the process comprises the conversion of an organic oxygenate-to-olefins or alkylamines.

12. The process of claim 10, wherein said sieve is a metalloaluminophosphate, silicoaluminophosphate, or aluminophosphate.

13. The process of claim 10, wherein said intracrystalline mesopores have a diameter of about 10 to about 50 nanometers.

14. The process of claim 10 and having a mesopore volume larger than 0.1 ml/g.

15. The process of claim 10 and having a mesopore volume larger than 0.2 ml/g.

16. The process of claim 1 or 10, wherein the nanoparticles of a removable material comprise carbon black.

* * * * *